(12) United States Patent
Smith et al.

(10) Patent No.: US 9,555,195 B2
(45) Date of Patent: Jan. 31, 2017

(54) DRIVE ASSEMBLY, DRIVE COMPONENT AND DRUG DELIVERY DEVICE

(75) Inventors: Christopher James Smith, Holmes Chapel (GB); Stephen David Butler, Essington (GB); Mark Philip Horlock, Timperley (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 981 days.

(21) Appl. No.: 13/701,995

(22) PCT Filed: Jun. 9, 2011

(86) PCT No.: PCT/EP2011/059567
§ 371 (c)(1),
(2), (4) Date: Apr. 9, 2013

(87) PCT Pub. No.: WO2011/154483
PCT Pub. Date: Dec. 15, 2011

(65) Prior Publication Data
US 2013/0211331 A1    Aug. 15, 2013

(30) Foreign Application Priority Data

Jun. 11, 2010  (EP) .................................... 10165640

(51) Int. Cl.
*A61M 5/142* (2006.01)
*A61M 5/315* (2006.01)
*F16H 19/02* (2006.01)

(52) U.S. Cl.
CPC ......... *A61M 5/31551* (2013.01); *A61M 5/142* (2013.01); *A61M 5/31555* (2013.01);
(Continued)

(58) Field of Classification Search
CPC ........................... A61M 5/31585; A61M 5/42; A61M 5/31555; A61M 2205/581; A61M 2205/582; Y10T 74/18568; F16H 19/02
See application file for complete search history.

(56) References Cited

U.S. PATENT DOCUMENTS

| 533,575 A | 2/1895 | Wilkens |
|---|---|---|
| 5,226,895 A | 7/1993 | Harris |
| (Continued) | | |

FOREIGN PATENT DOCUMENTS

| DK | WO 9938554 A1 * | 8/1999 | ........ A61M 5/31551 |
|---|---|---|---|
| EP | 0688571 A1 | 12/1995 | |
| | (Continued) | | |

OTHER PUBLICATIONS

International Search Report for Int. App. No. PCT/EP2011/059567, completed Aug. 29, 2011.
(Continued)

*Primary Examiner* — Theodore Stigell
*Assistant Examiner* — Amber Stiles
(74) *Attorney, Agent, or Firm* — McDonnell Boehnen Hulbert & Berghoff LLP

(57) ABSTRACT

A drive assembly for a drug delivery device comprises a rotation member being configured to be rotated in a first direction during setting of a dose of a drug and to be rotated in a second direction during delivery of the dose, a drive component being configured to follow rotational movement of the rotation member in the second direction during delivery of the dose and a stop member being configured to prevent rotational movement of the drive component in the first direction. The drive component comprises a first drive part and a second drive part, coupled to each other such that relative rotational movement of the first and second drive parts is prevented and relative axial movement is permitted.

80 Claims, 4 Drawing Sheets

(52) U.S. Cl.
CPC ......... *A61M 5/31585* (2013.01); *F16H 19/02* (2013.01); *A61M 2205/581* (2013.01); *A61M 2205/582* (2013.01); *Y10T 74/18568* (2015.01)

(56) References Cited

U.S. PATENT DOCUMENTS

| | | |
|---|---|---|
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michael |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,725,508 A | 3/1998 | Chanoch et al. |
| 5,827,232 A | 10/1998 | Chanoch et al. |
| 5,921,966 A | 7/1999 | Bendek et al. |
| 5,961,495 A | 10/1999 | Walters et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 2002/0120235 A1 | 8/2002 | Enggaard |
| 2004/0059299 A1 | 3/2004 | Moller |
| 2004/0210199 A1* | 10/2004 | Atterbury ......... A61M 5/31566 604/224 |
| 2006/0153693 A1* | 7/2006 | Fiechter ............ A61M 5/31553 417/63 |
| 2007/0021718 A1* | 1/2007 | Burren ................... A61M 5/24 604/110 |
| 2007/0123829 A1 | 5/2007 | Atterbury et al. |
| 2008/0287883 A1* | 11/2008 | Radmer ............ A61M 5/31551 604/211 |
| 2009/0153693 A1 | 6/2009 | Onuki et al. |
| 2009/0275916 A1 | 11/2009 | Harms et al. |

FOREIGN PATENT DOCUMENTS

| | | |
|---|---|---|
| EP | 0937471 A2 | 8/1999 |
| EP | 0937476 A2 | 8/1999 |
| EP | 1923085 | 5/2008 |
| EP | 1923085 A1 | 5/2008 |
| EP | 1974761 A2 | 10/2008 |
| EP | 2221077 A2 | 8/2010 |
| JP | H8-000730 A | 1/1996 |
| WO | 99/38554 | 8/1999 |
| WO | 9938554 A1 | 8/1999 |
| WO | 0110484 A1 | 2/2001 |
| WO | 2010066796 A1 | 6/2010 |

OTHER PUBLICATIONS

Form PCT/IB/326, Notification Concerning Transmittal International Preliminary Report on Patentability.
European Search Report issued in European Patent Application No. 10165640 dated Nov. 30, 2010.
English Translation of Notice of Reasons for Rejection issued in Japanese Patent Application No. 2013-513689 dated Mar. 24, 2015.

* cited by examiner

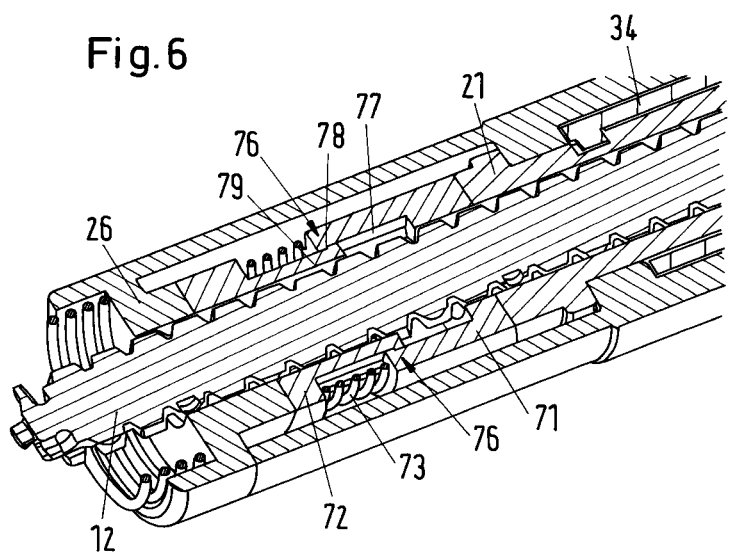

1

DRIVE ASSEMBLY, DRIVE COMPONENT AND DRUG DELIVERY DEVICE

CROSS REFERENCE TO RELATED APPLICATIONS

The present application is a U.S. National Phase Application pursuant to 35 U.S.C. §371 of International Application No. PCT/EP2011/059567 filed Jun. 9, 2011, which claims priority to European Patent Application No. 10165640.3 filed Jun. 11, 2010. The entire disclosure contents of these applications are herewith incorporated by reference into the present application.

FIELD OF INVENTION

The present disclosure relates to a drive assembly for a drug delivery device and a drug delivery device incorporating such a drive assembly.

BACKGROUND

A drug delivery device may comprise a cartridge containing a drug. For expelling a dose of the drug from the cartridge, a piston within the cartridge may be displaced in a distal direction by a piston rod. A drug delivery device is described in US 2007/0123829 A1, for example.

SUMMARY

It is an object of the present invention to provide a drive assembly, a drive component of a drive assembly and a drug delivery device, wherein an administration of a drug is improved.

According to one aspect, a drive assembly for a drug delivery device is provided. The drive assembly comprises a housing having a proximal end and a distal end. Furthermore, the drive assembly comprises a rotation member being configured to be rotated in a first direction with respect to the housing during setting of a dose of a drug and to be rotated in a second direction with respect to the housing during delivery of the dose, the second direction being opposite to the first direction. Moreover, the drive assembly comprises a drive component being configured to follow rotational movement of the rotation member in the second direction during delivery of the dose and a stop member being configured to prevent rotational movement of the drive component in the first direction with respect to the housing and to permit rotational movement of the drive component in the second direction with respect to the housing. The drive component comprises a first drive part and a second drive part, coupled to each other such that relative rotational movement of the first and second drive parts is prevented and relative axial movement of the first and second drive parts is permitted. Preferably, the first drive part is configured for engagement with the rotation member and the second drive part is configured for engagement with the stop member.

In this context, the term "housing" shall mean any exterior housing, interior housing or a part fixed to an exterior or interior housing such that a relative movement between this part and the exterior or interior housing is prevented. The housing may be designed to enable the safe, correct, and comfortable handling of the drug delivery device or any of its mechanisms. It may be designed to house, fix, protect, guide, and/or engage with any of the inner components of the drug delivery device, e.g., the drive assembly, cartridge, piston, piston rod. The housing may be unitary or a multipart component of tubular or non-tubular shape.

The term "distal end" designates that end of a drug delivery device or a component thereof which is or is to be arranged closest to a dispensing end of the drug delivery device. The term "proximal end" designates that end of the device or a component thereof which is or is to be arranged furthest away from the dispensing end of the device. Accordingly, the term "distal direction" designates the direction from the proximal end towards the distal end and the term "proximal direction" designates the direction from the distal end towards the proximal end.

The drug delivery device may be an injection device. The drug delivery device may be a pen-type device, in particular a pen-type injector. The device may be a disposable or a re-usable device. The device may be a fixed-dose device, where a user is disabled from selecting the size of a dose. Here, the absolute sizes of the doses to be dispensed are predetermined by the design of the device. The device may be configured such that each dose to be dispensed has the same size or such that the sizes of the doses vary. Alternatively, the device may be a variable-dose device, wherein the absolute size of a dose to be dispensed can be selected by a user. In particular, the user can choose between different dose sizes. The drug delivery device may be a manually, in particular a non-electrically, driven device.

Mechanical interaction of the stop member and the drive component, in particular of the stop member and the second drive part, may prevent rotational movement of the drive component with respect to the housing in the first direction and, in particular, with respect to the stop member during setting of the dose. Thus, rotation of the drive component during dose setting can be avoided. As examples, such a mechanical interaction may comprise interlocking, engagement and/or abutment, during rotation of the rotation member in the first direction. As an example, the second drive part may comprise a toothing for engagement with the stop member.

The drive assembly may comprise a piston rod being configured to be displaced in the distal direction for delivering a dose of a drug and being configured such that rotational movement of the drive component in the second direction is at least partially converted into movement of the piston rod in the distal direction with respect to the housing.

The term "piston rod" shall preferably mean a component adapted to operate through/within the housing, which may be designed to transfer axial movement through/within the drug delivery device, preferably from the drive component to the piston, for example for the purpose of discharging/dispensing an injectable product. Said piston rod may be flexible or not. It may be a simple rod, a lead-screw, a rack and pinion system, a worm gear system, or the like. The term "piston rod" shall further mean a component having a circular or non-circular cross-section. It may be made of any suitable material known by a person skilled in the art and may be of unitary or multipart construction.

The drive component may be coupled to the piston rod so as to at least partially convert the drive components rotational movement in the second direction into distal movement of the piston rod with respect to the housing. The drive component may be engaged with the piston rod such that relative axial movement between the piston rod and the drive component is allowed and relative rotational movement is prevented. In particular, the drive component, for example at least one of the first and second drive parts, may be engaged with the piston rod. The drive component may be in splined engagement with the piston rod.

The drive component may also be coupled to the piston rod such that a movement of the drive component in the first direction may be at least partially converted into a movement of the piston rod in the proximal direction with respect to the housing. Accordingly, the risk of the piston rod being moved in the proximal direction during dose setting can be reduced by preventing rotational movement of the drive component in the first direction during setting of the dose due to provision of the stop member. Unintentional proximal movement of the piston rod may result in decreased dose accuracy. Consequently, dose accuracy may be improved by preventing rotation of the drive component with respect to the housing during dose setting.

According to a preferred embodiment, the drive component and the rotation member are rotatable around a common rotation axis. The piston rod may be displaced in the distal direction with respect to the housing along the rotation axis. The rotation axis may run along the piston rod and, in particular, along a main direction of extent of the piston rod.

The drive component, in particular the first drive part and the second drive part, may be arranged between the stop member and the rotation member.

The rotational movement of the drive component in the second direction may be at least partially converted into rotational movement of the piston rod with respect to the housing, in particular rotational movement in the same direction and/or by the same angle, and movement of the piston rod with respect to the housing in the distal direction. The piston rod may be threadedly coupled to the housing, in particular threadedly engaged with the housing, for this purpose.

According to another embodiment, the rotational movement of the drive component is converted into pure linear movement of the piston rod in the distal direction. Accordingly, the piston rod may be moved in the distal direction without rotating with respect to the housing. It is particularly suitable for the drive component to comprise gear teeth for engaging the piston rod, for this purpose.

The drive assembly may comprise a dose member. The dose member is preferably movable with respect to the housing, for example during setting and delivery of a dose. The dose member may be movable in the proximal direction with respect to the housing for setting the dose. The dose member may be movable in the distal direction with respect to the housing for delivering the set dose. Movement of the dose member with respect to the housing may be converted into rotational movement of the rotation member with respect to the housing. Movement of the dose member for setting the dose may be converted into rotational movement of the rotation member with respect to the housing in the first direction. Movement of the dose member for delivering the set dose may be converted into rotational movement of the rotation member with respect to the housing in the second direction. The dose member may be secured against rotational movement with respect to the housing. The dose member may be splined to the housing, for example. The dose member may be movable with respect to the rotation member. Movement of the dose member with respect to the rotation member may be converted into rotational movement of the rotation member.

The dose member and the rotation member may be engaged, preferably threadedly engaged. As an example, rotational movement of the rotation member may be achieved by a threaded engagement which may convert linear movement of the dose member into rotational movement of the rotation member with respect to the housing.

According to a preferred embodiment, the first drive part, preferably permanently, abuts and/or engages the rotation member during rotational movement of the rotation member for setting and delivery of the dose. The second drive part may, preferably permanently, abut and/or engage the stop member during rotational movement of the rotation member for setting and delivery of the dose. In a preferred embodiment, the first drive part permanently abuts the rotation member and the second drive part permanently abuts the stop member.

According to a preferred embodiment, the drive component comprises a biasing member for providing a force on at least one of the first and second drive parts for keeping at least one of the first and second drive parts in abutment with at least one of the rotation member and the stop member. Preferably, the biasing member provides a force on both the first and second drive part to keep the first drive part in abutment with the rotation member and the second drive part in abutment with the stop member. As an example, the biasing member may be a spring member. Preferably, the biasing member abuts at least one of the first and second drive parts for providing a force on the respective drive part.

Preferably, thereby, the first drive part is held in permanent abutment with the rotation member and the second drive part is held in permanent abutment with the stop member during setting and delivery of the dose, in particular during rotational movement of the rotation member in the first direction and in the second direction.

The biasing member may be located between the first and second drive part. Here, at least a part of the first drive part is located at one end of the biasing member, for example its proximal end, and at least a part of the second drive part is located at the opposite end of the biasing member, for example its distal end. The biasing member may be integrated into the drive component such that the drive component comprising the first and second drive parts and the biasing member is provided as a pre-assembled component fittable into other parts of the drive assembly. Thereby, the number of separate components of the drive assembly may be reduced and the assembly process of the drive assembly may be improved.

The biasing member may abut, preferably permanently abut, at least one of the first and second drive parts. Preferably, the biasing member abuts both the first and second drive parts. Preferably, the biasing member may be configured such that it follows rotational movements of the first and second drive parts.

Preferably, the biasing member forces the first and second drive parts apart in opposite axial directions. Thereby, the first drive part may be forced onto the rotation member and the second drive part may be forced onto the stop member.

According to an embodiment, the stop member is secured against rotational movement with respect to the housing. According to a preferred embodiment, the stop member is secured against both axial and rotational movement with respect to the housing.

As examples, the stop member may be permanently fixed to the housing, for example may be designed as an insert fixed to the inner side of the housing, or may be an integral part of the housing.

In a preferred embodiment, the drive component and the rotation member are coupled, preferably permanently coupled, to one another by a uni-directional friction clutch mechanism. Preferably, here, the first drive part and the rotation member are coupled by the uni-directional friction clutch mechanism. This friction clutch mechanism may be configured to permit relative rotational movement between rotation member and drive component during movement of the rotation member for setting of the dose and to prevent relative rotational movement of rotation member and drive component during movement of the rotation member for delivery of the dose.

In a preferred embodiment, the drive component and the stop member are coupled, preferably permanently, to one another by a uni-directional friction clutch mechanism. Preferably, here, the second drive part and the stop member are coupled by the uni-directional friction clutch mechanism. This friction clutch mechanism may be configured to prevent relative rotational movement between the stop member and the drive component during movement of the rotation member for setting of the dose and to permit relative rotational movement of the stop member and the drive component during movement of the rotation member for delivery of the dose.

According to a preferred embodiment, at least one of the drive component, the stop member, the rotation member and the dose member may be formed as or may comprise a sleeve. A rod, for example the piston rod or an axis rod which defines the rotation axis may extend through one of, more of or all of drive sleeve, stop sleeve, rotation sleeve and dose sleeve.

Preferably, at least one of the first and second drive parts comprises a sleeve. The piston rod may extend through the sleeve. In a preferred embodiment, both drive parts comprise a sleeve. One of the sleeves may at least partially enclose the other sleeve. The sleeves may be slidably coupled to each other. As an example, the sleeve of the first drive part may partially enclose the sleeve of the second drive part.

The drive component may comprise retaining means to limit the axial separation of the first and second drive parts. The retaining means may be configured such that a complete separation of the first and second drive parts may be prevented in a state where the drive component is not assembled with other parts of the drive assembly.

As an example, the retaining means may be arranged at one of or both the first and second drive parts. The retaining means may comprise a first stop face on one of the drive parts arranged for abutment with a second stop face on the other drive part. The stop faces may be designed such that at a defined axial separation of the drive parts the stop faces abut and thereby prevent further separation of the drive parts.

According to a further aspect, there is provided a drive component for use in a drive assembly as described above, the drive component being provided as a pre-assembled component for assembly with the rotation member, the stop member and the housing for building the drive assembly. The drive component comprises a first drive part and a second drive part coupled to each other such that relative rotational movement of the first and second drive parts is prevented and relative axial movement is permitted. The first drive part may comprise first engagement means, e.g. a toothing. The first engagement means may be configured for establishing a uni-directional friction clutch mechanism which is adapted and arranged to prevent rotational movement of the first drive part in a first direction and to permit rotational movement of the first drive part in a second direction with respect to a mating first engagement means, e.g. a mating toothing. The second drive part may comprise second engagement means, e.g. a toothing, for establishing a uni-directional friction clutch mechanism which is adapted and arranged to prevent rotational movement of the second drive part in the first direction and to permit rotational movement of the second drive part in the second direction with respect to a second mating engagement means, e.g. a further toothing. The first drive part is configured for engagement with the rotation member of the drive assembly and the second drive part is configured for engagement with the stop member of the drive assembly.

In particular, the drive component may be configured such that in a state before the drive component is assembled with further parts of the drive assembly, a complete separation of any of its parts from the drive component, for example a falling away of a part, is prevented. For this aim, the drive component may comprise retaining means, for example retaining means as described above. The retaining means may prevent a complete separation of the first and second drive parts.

According to an embodiment, the first and the second engagement means are configured to face in opposite directions with respect to one another.

The first engagement means may comprise a first toothing comprising a plurality of teeth. The second engagement means may comprise a second toothing comprising a plurality of teeth. The first toothing may be oppositely arranged compared to the second toothing.

The first mating engagement means may comprise a first mating toothing comprising a plurality of teeth. The second mating engagement means may comprise a second mating toothing comprising a plurality of teeth. The first mating toothing may be oppositely arranged compared to the second mating toothing.

According to an embodiment, the drive component comprises a biasing member, e.g. a compression spring. The biasing member may be adapted and arranged to provide a force which tends to force the first and second drive parts away from each other in opposite axial directions.

The biasing member may be configured such that the first drive part is held in engagement with the rotation member during a delivery operation. The biasing member may be configured such that the second drive part is held in engagement with the stop member during a delivery operation.

In a preferred embodiment, the drive component comprises a biasing member as described above, which is part of the pre-assembled component. The biasing member may provide a force on at least one of the first and second drive parts. The biasing member may force the first and second drive parts apart in opposite axial directions. Preferably, the drive component is configured such that a complete separation, for example a falling away, of the biasing member from at least one of the first and second drive parts is prevented. As an example, the biasing member may be located between the first and second drive parts and may be held in place by the first and second drive parts. Additionally or alternatively, the drive component may comprise further retaining means for preventing a complete separation, for example a falling away, of the biasing member.

Features described above and below in connection with the drive assembly and the drive component may also be applied for the corresponding drive component which is provided as a pre-assembled component.

As an example, at least one of the first and second drive parts may comprise a toothing for engagement with at least one of the stop member and the rotation member. Preferably, both the first and second drive parts comprise a toothing. As an example, the first drive part may comprise a toothing at its proximal end and the second drive part may comprise a toothing at its distal end.

According to a further aspect, a drug delivery device is provided, the drug delivery device comprising at least one of the drive assembly and the drive component as described above. The device may comprise means for attaching a drug reservoir. The drug reservoir may be permanently or releasably attached to the housing of the device.

The term "drug" as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

BRIEF DESCRIPTION OF THE FIGURES

FIG. 6 schematically shows a more detailed view of a part of FIGS. 2 and 4.

Like elements, elements of the same kind and identically acting elements are provided with the same reference numerals in the figures.

DETAILED DESCRIPTION

Figure 1:
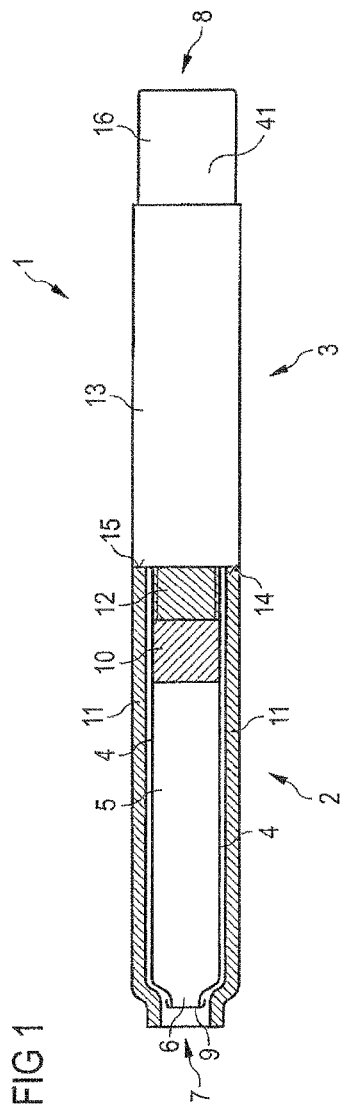
FIG. 1 schematically shows a partly sectional side view of an exemplary embodiment of a drug delivery device.

FIG. 1 shows a drug delivery device 1 having a distal end 7 and a proximal end 8. The device 1 comprises a cartridge part 2 and a drive part 3. The cartridge part 2 comprises a drug reservoir in form of a cartridge 4 retaining a drug 5, preferably a liquid drug. The cartridge 4 preferably comprises a plurality of doses of the drug 5. The drug 5 may comprise insulin, heparin, or growth hormones, for example.

The cartridge 4 has an outlet 6 at its distal end. The drug 5 can be dispensed from the cartridge through the outlet 6.

The device 1 may be a pen-type device, in particular a pen-type injector. The device 1 may be a disposable or a reusable device. The device 1 may be a fixed-dose device, wherein a user can not choose between different dose sizes, or a variable-dose device, wherein a user can choose between different dose sizes. The device 1 may be a needle-based or a needle free device. The device 1 may be an injection device.

The outlet 6 may be covered by a membrane 9, which protects the drug 5 against external influences during storage of the cartridge. For drug delivery, membrane 9 may be opened, e.g. pierced. For example, membrane 9 may be pierced by a needle unit (not explicitly shown). The needle unit may be attached, for example releasably attached, to the distal end of the cartridge part 2. The needle unit may provide for fluid communication from the inside of the cartridge 4 to the outside of the cartridge through outlet 6.

A piston 10 is retained within the cartridge 4. The piston 10 is movable with respect to the cartridge 4. The piston 10 may seal the drug 5 within the cartridge 4. The piston 10 expediently seals the interior of the cartridge 4 proximally. Movement of the piston 10 with respect to the cartridge 4 in the distal direction causes the drug 5 to be dispensed from the cartridge 4 through outlet 6 during operation of the device 1.

The cartridge part 2 furthermore comprises a cartridge retaining member 11, wherein the cartridge 4 is retained. The cartridge retaining member 11 may at least partially house the cartridge 4. The cartridge retaining member 11 may be provided with a fixing member (not explicitly shown) for attaching the cartridge part 2 to the drive part 3.

The cartridge part 2 and the drive part 3 are secured to one another, preferably releasably secured. A cartridge part 2 which is releasably secured to the drive part 3 may be detached from the drive part 3, for example in order to allow for replacing the cartridge 4. As an example, if all the doses of the drug retained in a cartridge 4 have been dispensed, the cartridge 4 may be removed and a new cartridge may be secured to the drive part 3. The cartridge retaining member 11 may be releasably secured to the drive part 3 via a thread, for example. Alternatively, the cartridge retaining member 11 may be dispensed with. It is particularly expedient, in this case, to apply a robust cartridge 4 and to attach the cartridge directly to the drive part 3.

The drive part 3 comprises a housing 13 which may be part of a drive assembly. A proximal end side 14 of the cartridge part 2 is secured to the drive part 3 at a distal end side 15 of the housing 13, for example via a threaded connection. Housing 13, cartridge 4 and/or cartridge retaining member 11 may have a tubular shape.

The drive part 3 is configured for transferring force, preferably user-exerted force, particularly preferably manually exerted force, to the piston 10 for displacing the piston 10 with respect to the cartridge 4 in the distal direction. A dose of drug 5 may be dispensed from the cartridge 4 in this way. The size of the delivered dose 5 may be determined by the distance by which the piston 10 is displaced with respect to the cartridge 4 in the distal direction.

The drive part 3 comprises a drive assembly comprising a piston rod 12. The piston rod 12 is configured for transferring force to the piston 10, thereby displacing the piston 10 in the distal direction with respect to the cartridge 4. A distal end face of the piston rod 12 is arranged to abut a proximal end face of the piston 10. A bearing member (not explicitly shown) may be arranged to advance the piston 10, preferably to abut the proximal end face of the piston 10. The bearing member may be located between piston 10 and piston rod 12. The bearing member may be secured to the piston rod 12 or a separate member. If the piston rod 12 is configured to be rotated during operation of the device 1, for example during dose delivery, it is particularly expedient to provide for a bearing member. The bearing member may be displaced together with the rotating piston rod 12 with respect to the housing 13. The piston rod 12 may be rotatable with respect to the bearing member. In this way, the risk that the rotating piston rod 12 drills into the piston 10 and thereby damages the piston 10 is reduced. Accordingly, while the piston rod 12 rotates and is displaced with respect to the housing 13, the bearing member is preferably only displaced, i.e. does not rotate. The piston rod 12 may be bounded by the bearing member.

The drive part 3 comprises a dose part 16. The dose part 16 is movable with respect to the housing 13. The dose part 16 may be movable in the proximal direction with respect to the housing 13 for setting a dose of the drug 5 which is to be delivered and may be movable in the distal direction with respect to the housing 13 for delivery of the set dose. The dose part 16 is preferably coupled to the housing 13. The dose part 16 may be secured against rotational movement with respect to the housing 13. The dose part 16 may be displaced from a distal end position to a proximal end position with respect to the housing 13 for setting a dose and from the proximal end position to the distal end position for delivering the dose (not explicitly shown). The distance by which the dose part 16 is displaced with respect to the housing 13 during setting of the dose may determine a size of the dose. The proximal end position and the distal end position may be determined by a respective stop feature which may limit the proximal or distal travel of the dose part 16 with respect to the housing. The dose part 16 may comprise a dose knob, which may be gripped by a user. The dose knob 41 may be arranged and connected to the dose part 16 at the proximal end of the dose part 16. Dose knob 41 and dose part 16 may be a unitary component.

The device 1 may be a manually, in particular non-electrically, driven device. The user-applied force which causes the dose part 16 to be moved with respect to the housing 13 in the distal direction for delivering a dose may be transferred to the piston rod 12 by other parts of the drive assembly. The drive assembly is preferably configured such that a movement of the piston rod 12 with respect to the housing 13 is prevented when the dose part 16 is moved for setting a dose, for example in the proximal direction with respect to the housing 13.

Embodiments of a drive assembly which are suitable to be provided in the drug delivery device 1 as described above are described in more detail in the following.

Figure 2:
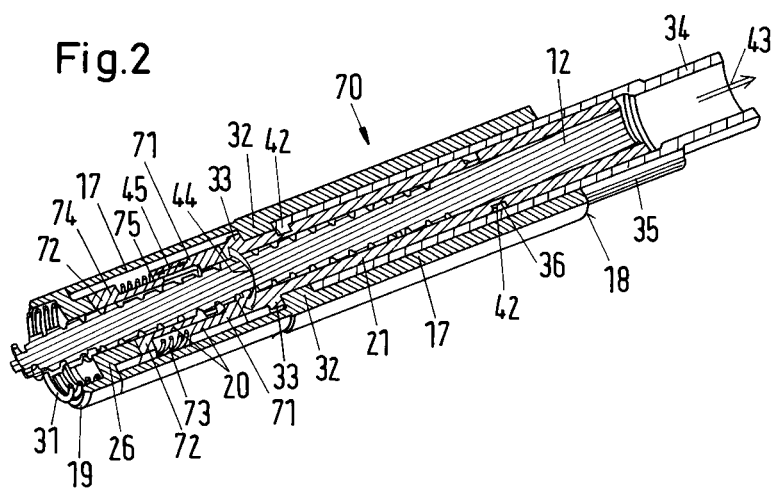
FIG. 2 schematically shows a perspective sectional view of a drive assembly with schematically indicated movements of elements during setting of a dose.
Figure 3:
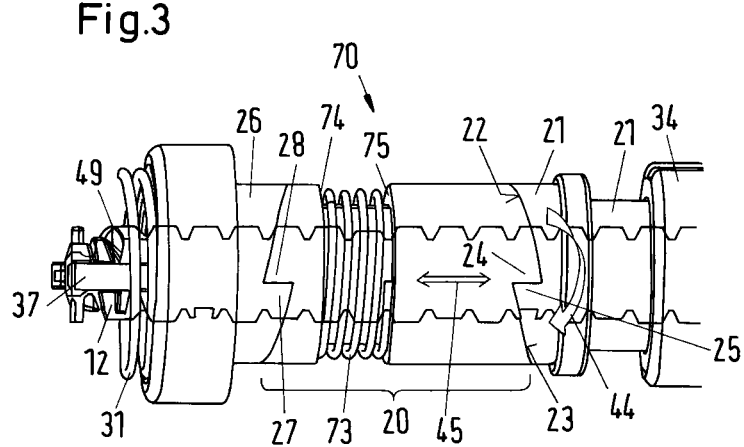
FIG. 3 schematically shows a more detailed side view of a part of FIG. 2.

FIG. 2 shows a perspective sectional view of a drive assembly 70 of the drive part 3 of the device 1. FIG. 6 shows a more detailed view of a part of FIG. 2. FIG. 3 shows a part of the drive assembly 70 of FIG. 2.

The drive assembly 70 comprises a housing part 17. The housing part 17 has a proximal end 18 and a distal end 19. The housing part 17 may be an outer housing 13 of the drive part 3 shown in FIG. 1, a part thereof or an insert within housing 13. The insert is secured against rotational and axial movement with respect to housing 13. The housing part 17 may be an insert sleeve, for example. The insert sleeve may be snap-fitted or glued to housing 13, for example. The housing part 17 has a tubular shape. Housing part 17 may comprise outer fixing elements (not explicitly shown), for example snap-fit elements, for fixing housing part 17 to housing 13.

The piston rod 12 is retained in the housing 13, in particular within the housing part 17. The piston rod 12 is driven in the distal direction with respect to the housing part 17 during dose delivery.

The drive assembly 70 furthermore comprises a drive component 20 retained within the housing part 17. The drive component 20 is configured to transfer force, preferably torque, to the piston rod 12. The transferred force causes the piston rod 12 to be displaced in the distal direction with respect to the housing part 17 for dose delivery.

The drive component 20 comprises a first drive part 71 and a second drive part 72, which are coupled to each other such that relative rotational movements with respect to each other are disabled and relative axial movements with respect to each other are allowed. As an example, the first drive part 71 may be in splined engagement with the second drive part 72. Here, one of the drive parts 71, 72 may have a guide slot 77 running in an axial direction, wherein an engagement feature 79 of the other drive part 71, 72, for example a guide lug may be guided (see FIG. 6).

Each of the first and the second drive parts 71, 72 comprises a sleeve, wherein the sleeve of the second drive part 72 is partially inserted into the sleeve of the first drive part 71. Both the first and second drive parts 71, 72 are axially displaceable relative to the housing part 17. The axial movement of the first and second drive parts 71, 72 relative to each other and relative to the housing 13 may compensate for play between components of the drive assembly 70 during operation.

The drive component 20 comprises a biasing member 73 in form of a helical spring member, in particular a compression spring. The biasing member 73 is biased during drug delivery operations of the drive assembly 70. The biasing member 73 provides for a force forcing the first and second drive parts 71, 72 apart from each other in opposite axial directions.

The biasing member 73 is located between a flange 74 at the distal end of the second drive part 72 and a distal end face 75 of the sleeve of the first drive part 71. The biasing member 73 is wound around the sleeve of the second drive part 72 and thus partially encloses the sleeve. The biasing member 73 abuts the flange 74 of the second drive part 72 and abuts the distal end face 75 of the sleeve of the first drive part 71 and thereby provides a separating force on the first and second drive parts 71, 72.

In further embodiments, the biasing member 73 may be coupled in a different way to the first and second drive parts 71, 72 for providing a separating force on the first and second drive parts 71, 72. As an example, the biasing member 73 may be arranged inside at least one of the first and second drive parts 71, 72. In this case, the biasing member 73 may abut a distal internal end face of the second drive part 72.

The drive component 20 may comprise retaining means 76 (see FIG. 6) limiting the relative axial separation of the first and second drive parts 71, 72. In particular, the first and second drive parts 71, 72 may comprise clip features or other retention features. As an example, a stop face 78 may be located at the distal end of a guide slot 77 in the first drive part 71 wherein an engagement feature 79 of the second drive part 72 is guided. At an axial separation of the first and second drive parts 71, 72 where the engagement feature 79 abuts the stop face 78, a further relative separation of the first and second drive parts 71, 72 may be prevented.

In a preferred embodiment, the drive component 20 is configured such that it is provided as a pre-assembled component before it is fitted into other parts of the drive assembly 70. Preferably, the drive component 20 comprises the biasing member 73, the first drive part 71 and the second drive part 72 coupled to each other such that disassembly from each other is prevented.

The drive component 20, comprising the first and second drive parts 71, 72 and the biasing member 73, is rotatable with respect to the housing part 17. The drive component 20, for example at least one of the first and second drive parts 71, 72, engages the piston rod 12. Thereby, rotational movement of the drive component 20, for example rotational movement in a second direction, is converted into distal movement of the piston rod 12 with respect to the housing part 17. This is explained in more detail below.

The drive assembly 70 furthermore comprises a rotation member 21. The rotation member 21 is rotatable with respect to the housing part 17 in a first direction, in particular for setting a dose of the drug, and in a second direction, in particular for delivering the set dose. The second direction is opposite to the first direction. The first direction may be counter-clockwise and the second direction may be clockwise as seen from the proximal end of the device 1, for example.

The first and second drive parts 71, 72 of the drive component 20, the rotation member 21 and the piston rod 12 are configured to be rotatable about a common rotation axis. The rotation axis extends through the drive component 20, the rotation member 21 and the piston rod 12. The rotation axis is the main longitudinal axis of the piston rod 12. The rotation axis runs between the proximal end and the distal end of the housing part 17.

The rotation member 21 is coupled to the drive component 20, in particular to the first drive part 71 of the drive component 20, by a uni-directional clutch mechanism, for example a friction clutch mechanism. This clutch mechanism permits rotational movement of the rotation member 21 with respect to the first drive part 71 when the rotation member 21 rotates in the first direction with respect to the housing part 17. The clutch mechanism prevents rotational movement of the rotation member 21 with respect to the first drive part 71, when the rotation member rotates in the second direction with respect to the housing part 17. Due to the coupling of the first and second drive parts 71, 72, the first and second drive parts 71, 72 may thus follow rotational movement of the rotation member 21 in the second direction with respect to the housing part 17.

The first drive part 71 is arranged to engage the rotation member 21 and, in particular, to abut the rotation member 21. The first drive part 71 comprises first engagement means 22, e.g. a toothing. The first drive part 71 comprises the toothing 22 at its proximal end. The rotating member 21 comprises first mating engagement means 23, e.g. a toothing. The rotation member 21 comprises the toothing 23 at its distal end which faces the first drive part 71. Toothing 22 comprises a plurality of teeth 24. Toothing 23 comprises a plurality of teeth 25. Toothings 22 and 23 are configured to mate with one another.

A respective tooth of teeth 24 and/or teeth 25 is ramp-shaped, in particular along the azimuthal direction as seen from the rotation axis. The ramp of the respective tooth is limited in the angular direction by a steep end face of that tooth, i.e. a face of the tooth that runs parallel to the rotation axis or includes a smaller angle with the rotation axis when projected on this axis than the ramp when projected on this axis. The steep end face is followed by the ramp of the next tooth.

The teeth 24 of the first drive part 71 may be circumferentially disposed on the first drive part 71, particularly at the end of the first drive part 71 which faces the rotation member 21. The teeth 25 may be circumferentially disposed on the rotation member 21, particularly at the end of the rotation member 21 which faces the first drive part 71.

When the steep end faces of two teeth abut and the rotation member 21 is rotated further on in the second direction, the steep sides stay in abutment and first drive part 71, thereby also the second drive part 72, follows the rotation of rotation member 21. When the rotation member 21 rotates in the first direction, the ramp of the teeth—which ramps, in particular, run obliquely with respect to the rotation axis—slide along each other and, in consequence, the rotation member 21 rotates with respect to the first drive part 71 and thereby, also with respect to the second drive part 72.

The drive assembly 70 furthermore comprises a stop member 26. The drive component 20 is arranged between the stop member 26 and the rotation member 21. The stop member 26 is configured for preventing rotational movement of the drive component 20 in the first direction with respect to the housing part 17 during setting of a dose, i.e. when the rotation member 21 rotates in the first direction. Thus, the rotation member 21 may rotate in the first direction with respect to the housing part 17, whereas the drive component 20 and the stop member 26 are prevented from rotating.

The stop member 26 is coupled to the second drive part 72 of the drive component 20 by another uni-directional clutch mechanism, in particular a friction clutch mechanism. This clutch mechanism prevents rotational movement of the second drive part 72, and thus, the drive component 20, with respect to the stop member 26 when the rotation member 21 rotates in the first direction with respect to the housing part 17. The clutch mechanism permits rotational movement of the second drive part 72, and thus, the drive component 20 with respect to the stop member 26, when the rotation member 21 rotates in the second direction with respect to the housing part 17.

Thus, the rotation member 21 may rotate with respect to the drive component 20 and the stop member 26 in the first direction during setting of a dose, wherein rotation of the drive component 20 is prevented by its interaction with the stop member 26. During delivery of the set dose, rotation member 21 as well as drive component 20 may rotate with respect to the stop member 26 in the second direction.

The stop member 26 is arranged to abut and/or engage the drive component 20 during setting of the dose and, preferably, during delivery of the dose. The stop member 26 comprises mating second engagement means 27, e.g. a toothing. The stop member 26 has the toothing 27 at one end which faces the second drive part 72 of the drive component 20, e.g. its proximal end. The teeth are ramp-shaped with a steep side and a less steep ramp. The teeth may be azimuthally disposed along the stop member, in particular on the perimeter of the stop member.

The second drive part 72 comprises second engagement means 28, e.g. a toothing. The second drive part 72 has the toothing 28 at one end which faces the stop member 26, e.g. its distal end. Toothings 22 and 28 of the drive component 20 are oppositely disposed. Toothing 28 may be configured in accordance to toothing 21 of the rotation member, i.e. may have the same shape and the same angular position relative to the rotation axis. Toothing 22 may be configured in accordance with toothing 27 of the stop member, i.e. may have the same shape and the same angular position relative to the rotation axis. Toothings 27 and 28, in particular the steep sides of the teeth, do cooperate, e.g. abut, for preventing rotation of the drive component 20 with respect to the housing part 17 and, in particular, with respect to the stop member 26 in the first direction.

The distance by which the first and second drive parts 71, 72 may be axially displaced with respect to each other or the housing 13 during dose setting and delivery operations may correspond to the maximum depth of a tooth of the respective toothing 22 or 28 of the drive component 20. Alternatively, the distance may be larger than the maximum depth of a tooth of the respective toothing.

The stop member 26 is secured against both rotational and axial movement with respect to the housing part 17. The stop member 26 may be integral with housing part 17 or an insert fixed to the housing part 17. The rotation member 21 may be secured against axial movement with respect to the housing part 17.

The biasing member 73 of the drive component 20 is biased during drug delivery operation of the drive assembly 70. The biasing member 73 provides a force that tends to keep the second drive part 72 of the drive component 20 in abutment with the stop member 26 and the first drive part 71 of the drive component in abutment with the rotation member 21. In particular, the biasing member 73 forces the first and second drive parts 71, 72 apart in opposite axial direction towards the rotation member 21 and the stop member 72, respectively.

The biasing member 73 keeps the second drive part 72 and the stop member 26 in permanent mechanical contact, for example abutment, with each other during setting and delivery of a dose of the drug. Additionally, the biasing member 73 keeps the first drive part 71 and the rotation member 26 in permanent mechanical contact, for example abutment, with each other during setting and delivery of a dose of the drug.

The drive assembly 70 furthermore comprises a support member 32. Support member 32 is expediently fixed against axial and rotational movement with respect to the housing part 17 or integrated into housing part 17. Support member 32 may be a protrusion, for example a ring-like protrusion. Rotation member 21 extends through an opening in support member 32 and may comprise a radially outwardly protruding member 33, for example a flange portion. The protruding member 33 is expediently provided for abutting support member 32, in particular the distal end side of support member 32. The support member 32 may provide for a counter force in the distal direction to the force which is exerted by the biasing member 73 on the first drive part 71 and thereby on the rotation member 21.

The stop member 26, which is secured against axial movement relative to the housing part 17, provides a counter force in the proximal direction to the force exerted by the biasing member 73 on the second drive part 72 and thereby on the stop member 26. Thereby, permanent abutment of the rotation member 21 with the first drive part 71 and permanent abutment of the stop member 26 with the second drive part 72 during setting and delivery of drug is facilitated.

The drive assembly 70 furthermore comprises a dose member 34. The dose member 34 may be dose part 16 or may be a part of the dose part 16 of FIG. 1. The dose member 34 is movable with respect to the housing in the proximal direction for setting of a dose and for delivery of the dose. For example, the dose member 34 may be moved in the proximal direction with respect to the housing part 17 during dose setting and in the distal direction with respect to the housing part 17 during dose delivery. The dose member 34 may engage the housing part 17 or, alternatively, another part of housing 13 (not explicitly shown). The dose member 34 is preferably secured against rotational movement with respect to the housing part 17. The dose member 34 may comprise a guide feature 35, for example a guide lug or a guide slot, that engages another guide feature, for example a guide slot or a guide lug, respectively, that is provided in the housing part 17 or the housing 13. Thereby, rotational movement of the dose member 34 can be prevented.

The dose member 34 may be moved in the proximal direction and in the distal direction with respect to rotation member 21. The dose member 34 is preferably permanently coupled to rotation member 21 such that movement of the dose member 34, e.g. in the proximal direction with respect to the housing part 17, for setting a dose of the drug is converted into rotational movement of the rotation member 21 in the first direction and movement of the dose member 34, e.g. in the distal direction with respect to the housing part 17, for delivering the dose is converted into rotational movement of the rotation member 21 in the second direction opposite to the first direction.

The rotation member 21 is provided with an outer thread 36. The thread 36 is engaged with one of or a plurality of engagement members 42 of the dose member 34. The respective engagement member is arranged on the inside of the dose member 34. The respective engagement member may be a thread or a part of a thread, for example. Thus, dose member 34 and rotation member 21 are threadedly coupled, in particularly threadedly engaged. The rotation member 21 is arranged inside the dose member 34. In other embodiments, the rotation member 21 may be arranged outside the dose member 34. The thread forms, in particular male and female thread forms, may be swapped, respectively.

The rotation member 21, the first drive part 71, the second drive part 72, the stop member 26 and the dose member 34 comprise a respective sleeve. The piston rod 12 is arranged to be driven and, in particular, is driven through the sleeves.

The drive component 20 and the piston rod 12 are configured such that rotational movement of the drive component 20 with respect to the housing 13 is converted into rotational movement of the piston rod 12 with respect to the housing 13. In particular, at least one of the first and second drive parts 71, 72 of the drive component 20 engages the piston rod 12, for example are in splined engagement with the piston rod. Preferably, both drive parts 71, 72 engage the piston rod. The piston rod 12 is displaceable with respect to the drive component 20 along a displacement axis running along the rotation axis.

The piston rod 12 comprises an engagement track 37, preferably two oppositely disposed engagement tracks, on the outside. The (respective) engagement track 37 may interrupt thread 49. The (respective) engagement track 37 preferably linearly extends along the axis along which the piston rod 12 is displaceable with respect to the housing 13 and, in particular, with respect to the drive component 20.

At least one of the first and second drive parts 71, 72 comprise a corresponding engagement track running in an axial direction, configured to be engaged with the engagement track 37 of the piston rod 12. The corresponding engagement track may be located at an inner surface of the second drive part 72 or the first drive part 71.

The piston rod 12 is threadedly coupled to the housing 13. The piston rod 12 may be provided with an outer thread 49, for example. The piston rod 12 may extend through and be engaged with a thread in an opening of a housing part which may be formed integrally with housing part 17, may be a housing part fixed thereto or may be a housing part secured separately from housing part 17 to housing 13. In the depicted embodiment, the opening is formed in the stop member 26. Thereby, the stop member 26 is threadedly engaged with the piston rod 12.

Rotational movement of the drive component 20 with respect to the housing 13 may thus be converted into rotational movement of the piston rod 12 with respect to the housing 13 and the rotational movement of the piston rod 12 is, on account of the threaded engagement of the piston rod 12 and a part of or a part secured to the housing 13, converted into movement of the piston rod 12 with respect to the housing 13 in the distal direction.

At the distal end of the drive assembly 70, a resilient member 31 is located. The resilient member 31 abuts a distal end face of the stop member 26 and is compressed by a cartridge or a cartridge retaining member when the cartridge is secured to the housing of the device. Thereby, the resilient member 31 pushes the cartridge towards the distal end of the cartridge retaining member.

In the following, operation of the present drive assembly 70 for delivering drug from the cartridge 4 of FIG. 1 is described.

FIGS. 2 and 3 show the drive assembly 70 with indicated movements of some of its elements during a dose setting operation.

To set a dose, a user may manually move dose member 34 in the proximal direction (arrow 43) with respect to the housing part 17. To do so, the user may grip a dose knob and pull it in the proximal direction. Dose member 34 moves proximally also with respect to the rotation member 21. Proximal movement of the rotation member 21 is prevented by support member 32 which abuts protruding member 33 of rotation member 21. Consequently, the proximal movement of dose member 34 with respect to the housing part 17 is converted into rotational movement of the rotation member 21 in the first direction (arrow 44) with respect to the housing part 17, in particular on account of the threaded engagement of dose member 34 and rotation member 21. Thus, the rotation member 21 rotates in the first direction—counter-clockwise as seen from the proximal end of the rotation member 21—with respect to the housing 13. Rotation member 21 also rotates with respect to the drive component 20 and to the stop member 26. The first and second drive parts 71, 72 of drive component 20 are prevented from rotating in the first direction by interaction with the stop member 26, e.g. by interlocking of toothings 27 and 28. As the piston rod 12 is coupled to the drive component 20 and rotation in the first direction of the drive component 20 would cause the piston rod 12 to travel in the proximal direction, the piston rod 12 is prevented from being driven in the proximal direction by interaction of stop member 26 and the second drive part 72 of drive component 20. By preventing the piston rod 12 from moving during dose setting dose accuracy can be increased.

When the rotation member 21 rotates in the first direction, the ramps of the teeth of toothing 23 of rotation member 21 slide along the ramps of the teeth of toothing 22. Thus, a tooth of the rotation member may index around the rotation axis until the tooth engages one of the next teeth of toothing 22 of the first drive part 71 of drive component 20. The teeth of rotation member 21 slide along the ramps of the teeth of the first drive part 71 of drive component 20. During this movement, the first drive part 71 is displaced in distal direction along the rotation axis with respect to piston rod 12 and housing 13 by a distance determined by, preferably equal to, the depth of a tooth of toothing 22, before a tooth of toothing 23 (totally) disengages that tooth of toothing 22. Thereby, the first drive part 71 also moves towards the second drive part 72. Afterwards, the tooth of the rotation member 21 engages the next tooth of toothing 22 and the force provided by biasing member 73 moves the first drive part 71 of drive component 20 back along the rotation axis into the axial start position. An according movement of the first drive part 71 of drive component 20 in the distal direction and back into the proximal direction is indicated by double arrow 45 in FIGS. 2 and 3.

A tooth of the rotation member 21 which engages the next tooth of the first drive part 71 of the drive component 20 may cause an audible and/or tactile feedback to the user.

The drive assembly 70 is suitable for a fixed dose device or a variable dose device. In a fixed dose device, the size of the fixed dose of drug to be delivered is preferably determined by the pitch of the thread 49 of the piston rod 12 and the number of teeth of the respective toothings 22, 28, 23, 27 in the drive component 20, rotation member 21 and stop member 26. In a variable dose device the increments in which a dose may be varied by a user are preferably determined by the pitch of the thread 49 of the piston rod 12 and the number of teeth of the respective toothings 22, 28, 23, 27 in the drive component 20, rotation member 21 and stop member 26. The rotation member 21 may be rotated over more than one tooth (dose increment) of the first drive part 71 of the drive component 20 for a user-settable dose device and over one tooth only for a fixed dose device. The number of teeth and size of the angular range of a tooth in the first drive part 71 of drive component 20 over which the rotation member 21 rotates during dose setting determines the size of the dose which is actually delivered. The dose member 34 and the rotation member 21 may be adapted to one another such that the rotation member 21 may rotate only by one tooth for a fixed dose device and by more than one tooth for a user-settable dose device.

Figure 4:
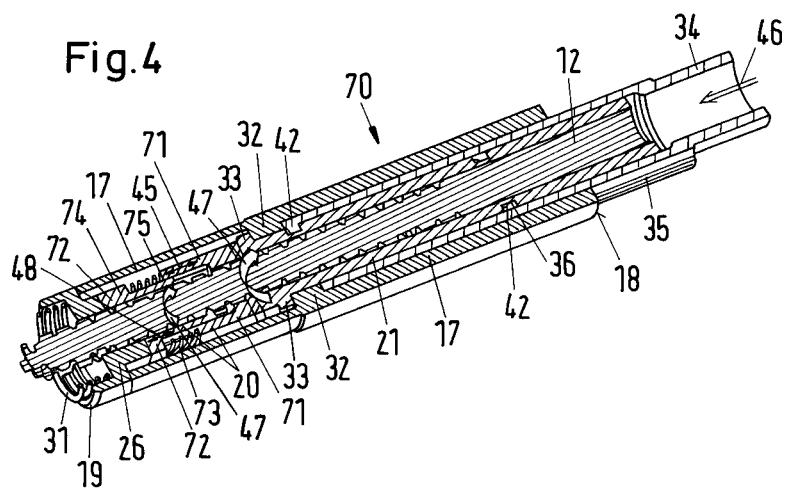
FIG. 4 schematically shows a perspective sectional view of a drive assembly with schematically indicated movements of elements during delivering a dose.
Figure 5:
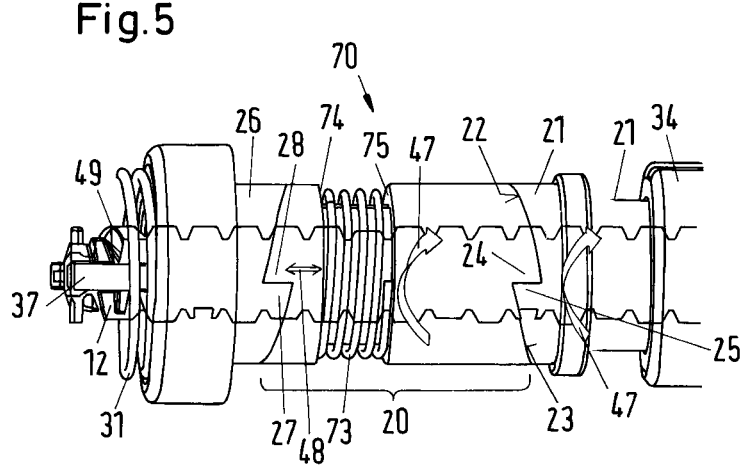
FIG. 5 schematically shows a more detailed side view of a part of FIG. 4.

FIGS. 4 and 5 show the drive assembly 70 with indicated movements of some of its elements during a dose delivery operation.

After the dose has been set, the dose part 16 and with it the dose member 34 is moved (pushed) by the user in the distal direction with respect to housing part 17 (arrow 46). Thus, the dose member 34 is moved in the distal direction with respect to the housing part 17. The rotation member 21 accordingly rotates in the second direction, which is opposite to the first direction, with respect to the housing (arrow 47). The first and second drive parts 71, 72 of drive component 20 follow rotational movement of the rotation member 21 in the second direction. Rotational movement of the drive component 20 in the second direction is converted into rotational movement of the piston rod 12 in the second direction, which movement, in turn, is converted into movement of the piston rod 12 in the distal direction. Accordingly, the piston 10 of FIG. 1 may be displaced in the distal direction with respect to the cartridge 4 and a dose of drug 5 is dispensed from the cartridge the amount of which corresponds to the previously set dose.

During dose delivery, toothings 22 of the first drive part 71 and toothings 23 of the rotation member 21 interlock and ramps of the teeth of toothing 28 of the second drive part 72 slide along ramps of the teeth of toothing 27 of stop member 26. This movement is similarly as described above for the relative rotational movement of rotation member and drive component with opposite rotation direction. The second part 72 of drive component 20 is thereby displaced in the proximal direction with respect to the stop member 26 by a distance corresponding to the depth of a tooth of toothing 27 in stop member 26. Biasing member 73 forces the second drive part 72 back into the axial starting position, when the next tooth of toothing 28 is engaged by the respective tooth of toothing 27 (double arrow 48).

A tooth of second drive part 72 of the drive component 20 which engages the next tooth of the stop member 26 may cause an audible and/or tactile feedback to the user.

The invention claimed is:

1. A drive assembly for a drug delivery device, the drive assembly comprising:
   a housing having a proximal end and a distal end,
   a rotation member being configured
      to be rotated in a first direction with respect to the housing during setting of a dose of a drug and
      to be rotated in a second direction with respect to the housing during delivery of the dose,
      the second direction being opposite to the first direction,
   a drive component being configured to follow rotational movement of the rotation member in the second direction during delivery of the dose,
   a stop member being configured to prevent rotational movement of the drive component in the first direction with respect to the housing and to permit rotational movement of the drive component in the second direction with respect to the housing, and
   a resilient member disposed at a distal end of the drive assembly,
   wherein the drive component comprises a first drive part and a second drive part,
   coupled to each other such that relative rotational movement of the first and second drive parts is prevented and relative axial movement is permitted,
   wherein the first drive part i) is configured to be coupled with the rotation member and ii) comprises a plurality of teeth near the proximal end, the teeth forming a part of a first uni-directional friction clutch mechanism, the first drive part and the rotation member being permanently coupled by the first uni-directional friction clutch mechanism, and
   the second drive part is configured for engagement with the stop member.

2. The drive assembly of claim 1, comprising a piston rod being configured to be displaced in the distal direction for delivering a dose of a drug and being configured such that rotational movement of the drive component in the second direction is at least partially converted into movement of the piston rod in the distal direction with respect to the housing.

3. The drive assembly of claim 1, wherein the drive component comprises a biasing member for providing a force on at least one of the first and second drive parts for keeping at least one of the first and second drive parts in abutment with at least one of the rotation member and the stop member.

4. The drive assembly of claim 3, wherein the biasing member forces the first and second drive parts apart in opposite axial directions.

5. The drive assembly of claim 3, wherein in an axial direction the biasing member is located between the first and second drive part.

6. The drive assembly of claim 1, wherein the drive component comprises a retaining means to limit the axial separation of the first and second drive parts.

7. The drive assembly of claim 2, wherein the drive component is engaged with the piston rod such that relative axial movement between the piston rod and the drive component is allowed and relative rotational movement is prevented.

8. The drive assembly of claim 1, wherein at least one of the first and second drive parts comprises a toothing for engagement with at least one of the rotation member and the stop member.

9. The drive assembly of claim 1, wherein the stop member is secured against both axial and rotational movements with respect to the housing.

10. The drive assembly of claim 1, wherein the stop member and the drive component are coupled to one another by a second uni-directional friction clutch mechanism, which is configured to prevent relative rotational movement between the stop member and the drive component in the first direction with respect to the housing and to permit relative rotational movement of the stop member and the drive component in the second direction with respect to the housing.

11. The drive assembly of claim 1, wherein the drive component and the rotation member are coupled to one another by the first uni-directional friction clutch mechanism, which is configured to permit relative rotational movement between the rotation member and the drive component during rotation of the rotation member in the first direction for setting of the dose and to prevent relative rotational movement of the rotation member and the drive component during rotation of the rotation member in the second direction for delivery of the dose.

12. The drive assembly of claim 1, comprising a dose member which is moveable with respect to the housing and wherein movement of the dose member with respect to the housing is converted into rotational movement of the rotation member with respect to the housing.

13. The drive assembly of claim 12, wherein the dose member is secured against rotational movement with respect to the housing.

14. The drive assembly of claim 1, wherein the first drive part comprises first engagement means which are configured for establishing the first uni-directional friction clutch mechanism which is adapted and arranged to prevent rotational movement of the first drive part in a first direction and to permit rotational movement of the first drive part in a second direction with respect to a mating first engagement means, and wherein the second drive part comprises second engagement means for establishing a second uni-directional friction clutch mechanism which is adapted and arranged to prevent rotational movement of the second drive part in the first direction and to permit rotational movement of the second drive part in the second direction with respect to a second mating engagement means.

15. The drive assembly of claim 14, wherein the first and the second engagement means are configured to face in opposite directions with respect to one another.

16. The drive assembly of claim 14, further comprising a biasing member which is adapted and arranged to provide a force forcing the first and second drive parts apart from each other in opposite axial directions.

17. The drive assembly of claim 14, wherein the drive component is provided as a pre-assembled component for assembly with the rotation member, the stop member and the housing for building the drive assembly.

18. A drug delivery device comprising at least one of the drive assembly according to claim 1, further comprising means for attaching a drug reservoir.

19. The drive assembly of claim 1,
wherein the first drive part is in splined engagement with the second drive part.

20. The drive assembly of claim 1,
wherein either the first drive part or the second drive part comprises a guide slot running in an axial direction.

21. The drive assembly of claim 20,
wherein either the first drive part or the second drive part comprises an engagement feature that is guided within the guide slot running in the axial direction.

22. The drive assembly of claim 1,
wherein the first drive part comprises a sleeve, and
wherein the second drive part is at least partially inserted into the first drive part.

23. The drive assembly of claim 1,
wherein the rotation member is arranged to abut the first drive part.

24. The drive mechanism of claim 1,
wherein the plurality of teeth are circumferentially disposed on the first drive part.

25. The drive assembly of claim 1,
wherein the rotation member further comprises a first mating engagement mechanism at an end which faces the first drive part.

26. The drive assembly of claim 25,
wherein the first mating engagement mechanism of the rotation member comprises toothing, and
wherein the toothing of the first mating engagement mechanism comprises a plurality of teeth.

27. The drive assembly of claim 7,
wherein the piston rod comprises a component comprising a circular cross section.

28. The drive assembly of claim 1,
wherein a rotational movement of the drive component is converted into axial movement of a piston rod in a distal direction without rotating with respect to the housing.

29. The drive assembly of claim 1,
wherein the stop member is secured against rotational movement with respect to the housing.

30. The drive assembly of claim 1,
wherein the stop member is secured against both axial and rotational movement with respect to the housing.

31. The drive assembly of claim 1,
the stop member is fixed to the housing.

32. The drive assembly of claim 1,
wherein the stop member is designed as an insert fixed to an inner side of the housing.

33. The drive assembly of claim 1,
wherein the stop member comprises a sleeve.

34. The drive assembly of claim 1,
wherein a piston rod extends through the rotation member, the first drive part, and the stop member.

35. The drive assembly of claim 1, wherein the resilient member abuts a distal end face of the stop member and is compressed by a cartridge or a cartridge retaining member.

36. The drive assembly of claim 1, wherein the stop member comprises one or more teeth that extend axially and engage with one or more teeth extending axially from the second drive part.

37. The drive assembly of claim 36, wherein the teeth of the stop member and the teeth of the second drive part prevent relative rotation of the stop member and the second drive part during dose setting.

38. The drive assembly of claim 1, further comprising a dose setting member which is movable axially relative to the housing and is rotationally fixed to the housing.

39. The drive assembly of claim 38, wherein the dose setting member comprises an internal thread that engages with an external thread of the rotation member.

40. A drive assembly for a drug delivery device, the drive assembly comprising:
a housing having a proximal end and a distal end,
a rotation member being configured
to be rotated in a first direction with respect to the housing during setting of a dose of a drug and
to be rotated in a second direction with respect to the housing during delivery of the dose,
the second direction being opposite to the first direction,
a drive component being configured to follow rotational movement of the rotation member in the second direction during delivery of the dose,
a stop member being configured to prevent rotational movement of the drive component in the first direction with respect to the housing and to permit rotational movement of the drive component in the second direction with respect to the housing, and
a resilient member disposed at a distal end of the drive assembly,
wherein the drive component comprises a first drive part and a second drive part,
coupled to each other such that relative rotational movement of the first and second drive parts is prevented and relative axial movement is permitted,
wherein the first drive part i) is configured for engagement with the rotation member and ii) comprises a plurality of teeth near the proximal end, the teeth forming a first uni-directional friction clutch mechanism with the rotation member, the teeth arranged to engage the rotation member during setting of the dose and during delivery of the dose, and
the second drive part is configured for engagement with the stop member.

41. The drive assembly of claim 40, comprising a piston rod being configured to be displaced in the distal direction for delivering a dose of a drug and being configured such that rotational movement of the drive component in the second direction is at least partially converted into movement of the piston rod in the distal direction with respect to the housing.

42. The drive assembly of claim 40, wherein the drive component comprises a biasing member for providing a force on at least one of the first and second drive parts for keeping at least one of the first and second drive parts in abutment with at least one of the rotation member and the stop member.

43. The drive assembly of claim 42, wherein the biasing member forces the first and second drive parts apart in opposite axial directions.

44. The drive assembly of claim 42, wherein in an axial direction the biasing member is located between the first and second drive part.

45. The drive assembly of claim 40, wherein the drive component comprises a retaining means to limit the axial separation of the first and second drive parts.

46. The drive assembly of claim 41, wherein the drive component is engaged with the piston rod such that relative axial movement between the piston rod and the drive component is allowed and relative rotational movement is prevented.

47. The drive assembly of claim 40, wherein at least one of the first and second drive parts comprises a toothing for engagement with at least one of the rotation member and the stop member.

48. The drive assembly of claim 40, wherein the stop member is secured against both axial and rotational movements with respect to the housing.

49. The drive assembly of claim 40, wherein the stop member and the drive component are coupled to one another by a second uni-directional friction clutch mechanism, which is configured to prevent relative rotational movement between the stop member and the drive component in the first direction with respect to the housing and to permit relative rotational movement of the stop member and the drive component in the second direction with respect to the housing.

50. The drive assembly of claim 40, wherein the drive component and the rotation member are coupled to one another by the first uni-directional friction clutch mechanism, which is configured to permit relative rotational movement between the rotation member and the drive component during rotation of the rotation member in the first direction for setting of the dose and to prevent relative rotational movement of the rotation member and the drive component during rotation of the rotation member in the second direction for delivery of the dose.

51. The drive assembly of claim 40, comprising a dose member which is moveable with respect to the housing and wherein movement of the dose member with respect to the housing is converted into rotational movement of the rotation member with respect to the housing.

52. The drive assembly of claim 51, wherein the dose member is secured against rotational movement with respect to the housing.

53. The drive assembly of claim 40, wherein the first drive part comprises first engagement means which are configured for establishing the first uni-directional friction clutch mechanism which is adapted and arranged to prevent rotational movement of the first drive part in a first direction and to permit rotational movement of the first drive part in a second direction with respect to a mating first engagement means, and wherein the second drive part comprises second engagement means for establishing a uni-directional friction clutch mechanism which is adapted and arranged to prevent rotational movement of the second drive part in the first direction and to permit rotational movement of the second drive part in the second direction with respect to a second mating engagement means.

54. The drive assembly of claim 53, wherein the first and the second engagement means are configured to face in opposite directions with respect to one another.

55. The drive assembly of claim 53, further comprising a biasing member which is adapted and arranged to provide a force forcing the first and second drive parts apart from each other in opposite axial directions.

56. The drive assembly of claim 53, wherein the drive component is provided as a pre-assembled component for assembly with the rotation member, the stop member and the housing for building the drive assembly.

57. A drug delivery device comprising at least one of the drive assembly according to claim 40, further comprising means for attaching a drug reservoir.

58. The drive assembly of claim 40,
wherein the first drive part is in splined engagement with the second drive part.

59. The drive assembly of claim 40,
wherein either the first drive part or the second drive part comprises a guide slot running in an axial direction.

60. The drive assembly of claim 59,
wherein either the first drive part or the second drive part comprises an engagement feature that is guided within the guide slot running in the axial direction.

61. The drive assembly of claim 40,
wherein the first drive part comprises a sleeve, and
wherein the second drive part is at least partially inserted into the first drive part.

62. The drive assembly of claim 40,
wherein the rotation member is arranged to abut the first drive part.

63. The drive mechanism of claim 40,
wherein the plurality of teeth are circumferentially disposed on the first drive part.

64. The drive assembly of claim 40,
wherein the rotation member further comprises a first mating engagement mechanism at an end which faces the first drive part.

65. The drive assembly of claim 64,
wherein the first mating engagement mechanism of the rotation member comprises toothing, and
wherein the toothing of the first mating engagement mechanism comprises a plurality of teeth.

66. The drive assembly of claim 41,
wherein the piston rod comprises a component comprising a circular cross section.

67. The drive assembly of claim 40,
wherein a rotational movement of the drive component is converted into axial movement of a piston rod in a distal direction without rotating with respect to the housing.

68. The drive assembly of claim 40,
wherein the stop member is secured against rotational movement with respect to the housing.

69. The drive assembly of claim 40,
wherein the stop member is secured against both axial and rotational movement with respect to the housing.

70. The drive assembly of claim 40,
the stop member is fixed to the housing.

71. The drive assembly of claim 40,
wherein the stop member is designed as an insert fixed to an inner side of the housing.

72. The drive assembly of claim 40,
wherein the stop member comprises a sleeve.

73. The drive assembly of claim 40,
wherein a piston rod extends through the rotation member, the first drive part, and the stop member.

74. The drive assembly of claim 40, wherein the resilient member abuts a distal end face of the stop member and is compressed by a cartridge or a cartridge retaining member.

75. The drive assembly of claim 40, wherein the stop member comprises one or more teeth that extend axially and engage with one or more teeth extending axially from the second drive part.

76. The drive assembly of claim 40, further comprising a dose setting member which is movable axially relative to the housing and is rotationally fixed to the housing.

77. The drive assembly of claim 76, wherein the teeth of the stop member and the teeth of the second drive part prevent relative rotation of the stop member and the second drive part during dose setting.

78. The drive assembly of claim 40, wherein the teeth of the first drive part are arranged to directly engage with the rotation member.

79. The drive assembly of claim 78, wherein the dose setting member comprises an internal thread that engages with an external thread of the rotation member.

80. The drive assembly of claim 40, wherein the teeth of the first drive part are arranged to engage teeth of the rotation member.

* * * * *